United States Patent [19]

Clayman

[11] 4,199,882
[45] Apr. 29, 1980

[54] PERSON AND BLOOD IDENTIFICATION WRIST BAND

[76] Inventor: Ralph V. Clayman, 716-13th Ave. SE., Minneapolis, Minn. 55414

[21] Appl. No.: 911,714

[22] Filed: Jun. 2, 1978

[51] Int. Cl.² ................................................ G09F 3/02
[52] U.S. Cl. .................................... 40/21 C; 128/771
[58] Field of Search ................ 40/21 C, 21 R, 2.2; 128/2 F, 2 G, DIG. 5, 214 R, 272

[56] References Cited

U.S. PATENT DOCUMENTS

| | | | |
|---|---|---|---|
| 2,911,743 | 11/1959 | Pokras | 40/21 C |
| 3,698,383 | 10/1972 | Baucom | 128/214 R X |
| 3,818,897 | 6/1974 | Smith | 128/2 F |
| 4,078,660 | 3/1978 | Lerro | 40/21 C X |

*Primary Examiner*—John F. Pitrelli
*Attorney, Agent, or Firm*—Wicks & Nemer

[57] ABSTRACT

A person and blood identification wrist band including a wrist band having a transparent pocket for a first identification tag of person and blood type. A blood container removably attached to the wrist band and having a transparent pocket on the blood container for a second identification tag identical to the first tag. The blood container has a pierceable membrane for filling the container with blood from a syringe. When the blood container is removed with its identification tag from the wrist band the identical first identification tag on the wrist band is visible.

7 Claims, 5 Drawing Figures

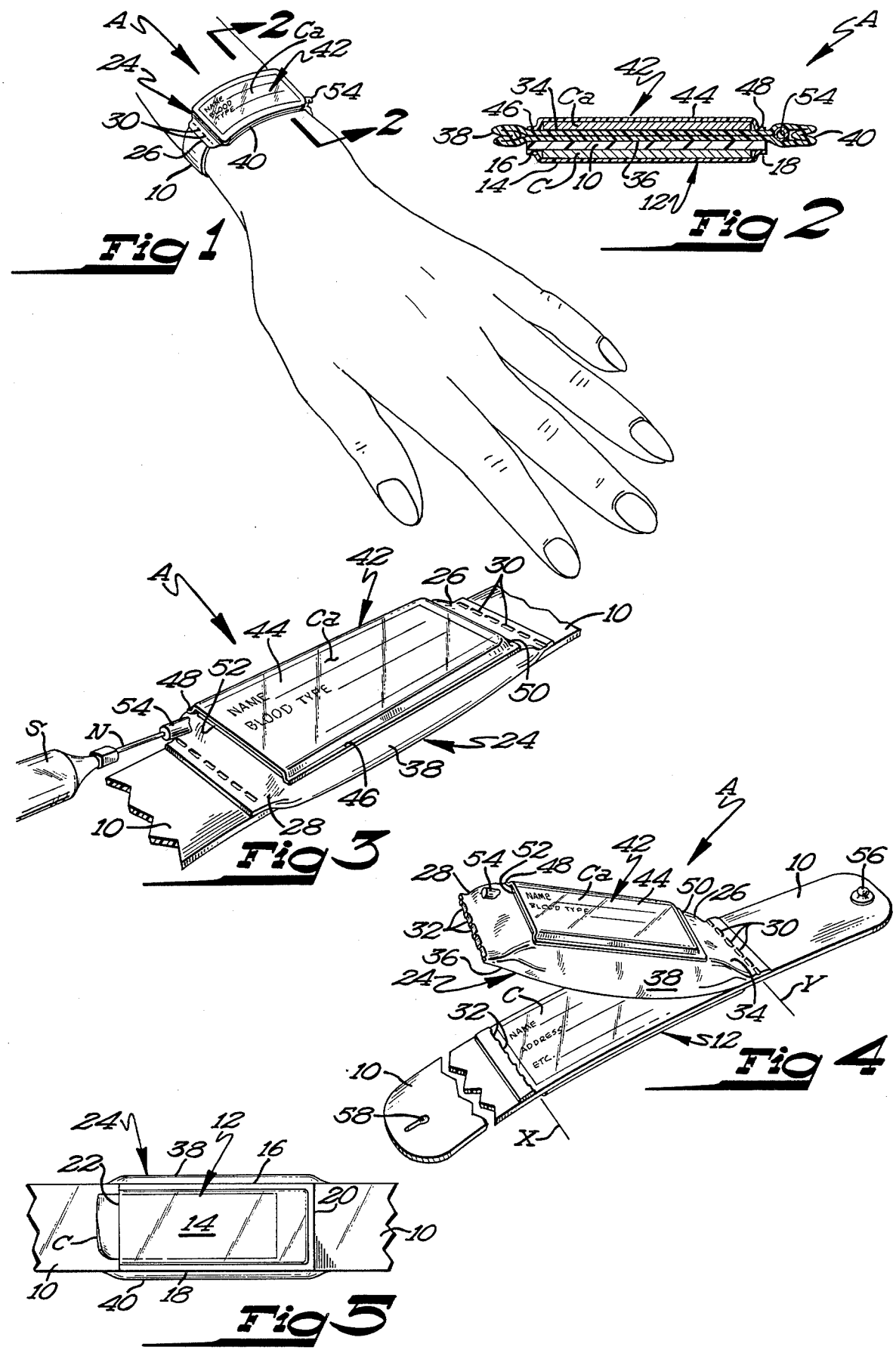

PERSON AND BLOOD IDENTIFICATION WRIST BAND

SUMMARY

The invention relates broadly to an improvement in a hospital identification wrist band.

Upon the admission of a patient to a hospital he is given an identification wrist band. When a blood sample is taken there exists the possibility of the blood sample not being identified or labeled as that of the patient. If such a mistake is made and the wrong blood type is given the patient postoperatively or in other situations, disastrous results may occur in irreversible renal failure or death. To obviate the above the following invention is provided.

It is an object of the invention to provide a wrist band having a first pocket for a first identification tag which includes blood type and other pertinent information. With the present device the patient's blood type is labeled upon a first identification tag upon admission and before the blood is received in the blood bank. The tag is visible through a transparent portion of the wrist band forming the first pocket.

A blood container is removably secured to the wrist band and a second tag pocket is formed on the top of the blood container having a transparent portion. A second identification tag identical to the first tag is inserted into the second tag pocket on the blood container and is visible through a transparent portion of the second pocket.

The blood bag is filled by means of a conventional syringe through a self-sealing membrane on the container when the bag is removed from the wrist band. The first and second identification tags are inserted into the respective pockets of the band and the blood container at the same time when the patient is admitted. With the blood container subsequently removed, it carries with it identification associated positively with the patient whereby there is little or no chance for any subsequent blood mismatching.

The invention will appear more clearly from the following detailed description when taken in connection with the accompanying drawings, showing by way of example a preferred embodiment of the inventive idea wherein like numerals refer to like parts throughout.

In the drawings forming part of this application:

FIG. 1 is a perspective view of a hospital identification wrist band having a separable identification container for blood embodying the invention and shown in position on a user's wrist.

FIG. 2 is a transverse section through the wrist band on the line 2—2 of FIG. 1.

FIG. 3 is a perspective view of the band with an illustration of the filling of the blood container.

FIG. 4 is a perspective view of the blood container in the process of being removed from the wrist band.

FIG. 5 is a bottom plan view of the band, portions of which are broken away.

Referring to the drawings in detail, the wrist band A includes a support in the form of the wrist band member 10 which has secured to the under surface thereof the identification tag cover 12. The band is transparent plastic at least at the area of the tag cover 12 from "X" to "Y", particularly FIG. 4. The tag cover 12 includes a strip of plastic 14 substantially the width of the band 10, and the strip is heat sealed along the longitudinal edges as at 16 and 18 and the end as at 20 to the underside of the wrist band which forms a pocket-like formation or tag cover with an open end as at 22. A first identification tag C with blood type and personal information thereof is slipped into the open end 22 of the tag cover and into the tag cover 12, indicia on the tag being visible through the transparent portion of the band 10, particularly FIG. 4.

The numeral 24 deisgnates a somewhat flexible plastic blood sample container formed with the flattened end portions 26 and 28. The end portion 26 is formed with the perforations 30 to weaken the connection and is heat sealed to the top of band 10, particularly FIG. 4. The other end portion 28 of the blood bag is also formed with perforations 32 to weaken the connection and is heat sealed to the top of band 10, said end 28 having been severed at the perforations as illustrated in FIG. 4.

The blood container is formed of the top and bottom walls 34 and 36, respectively joined by bellowed side walls 38 and 40, the top, bottom and side walls at each end blending into the end portions 26 and 28. A cover 42 is made of a sheet 44 of clear plastic which is heat sealed at its side edges as at 46 and 48 to the top wall 34 of the blood bag and heat sealed at one end at 50 to the blood container top wall 34 to thereby form a pocket. With the other end of the cover 42 open as at 52, the identification tag Ca, which is identical to the tag C, is easily slipped into the cover 42 from the open end 52 where it is visible through the clear plastic cover sheet 44 on top of the blood container.

Formed as part of and extending from the blood container is the filler tube 54 the outer sealed end of which is a membrane which is pierced by a needle N of a conventional syringe S for transferring blood from the syringe into the blood container. The sealed end of tube 54 is self sealing. On one end of the wrist band 10 is the button 56 which is forced through the slit 58 formed on the other end of band for securing the wrist band on the wrist of a user.

OPERATION

The band A is used as follows: Upon admission to a hospital the patient is supplied with a band A, and the identification tag C is filled in and inserted into the cover 12 from the open end 22 whereby the identification inidica on the tag is clearly visible through the transparent portion of the band 10 when the blood container 24 is removed as hereinafter explained. Also at the time of admission the blood identification tag Ca, identical to tag C, is filled in and slipped into the cover 42 on the outside of blood bag 24. When a blood sample is taken from the patient by such means as the syringe S, it is transferred into the blood container 24 by means of the filler tube 54. With the above preparation of the device A the blood container is removed when needed by simply breaking it off at the perforations 30 and 32 of the blood container. With the container removed the identification tag C on the wrist band is visible and the blood container carries with it the correct and identical identification tag Ca. If both tags C and Ca are correctly filled out at the same time and inserted in the band holders there is little chance of a mistake as to blood typing.

Having thus described the invention, what is claimed as new and desired to be secured by Letters Patent is:

1. A device for identification of a person and his related blood sample comprising:

(a) a support,
(b) a first identification tag,
(c) means for mounting said first identification tag on said support,
(d) a container for blood,
(e) a second identification tag identical to said first tag,
(f) means for mounting said second identification tag on said blood container parallely disposed to and in alignment with said blood container,
(g) means for removably connecting said blood container on said support parallely disposed to and in alignment with said first tag,
(h) means for filling said blood container with blood, and
(i) means for mounting said support on the person of a user.

2. The device of claim 1 in which
(a) said support is a band having
(b) means for engagement of the band about the wrist of the user.

3. The device of claim 2 in which said means for mounting said first identification tag on said support includes a pocket into which said tag is inserted.

4. The device of claim 1 in which said means for mounting said first identification tag on said support includes a pocket into which said tag is inserted.

5. The device of claim 3 in which said means mounting said second identification tag on said blood container includes a pocket into which said tag is inserted.

6. The device of claim 5 in which said means for removably connecting said blood container on said support includes weakened breakable areas of the connection.

7. A device for identification of a person and his related blood sample comprising:
(a) a support,
(b) a first identification tag,
(c) means for mounting said first identification tag on said support,
(d) a container for blood,
(e) a second identification tag identical to said first tag,
(f) means for mounting said second identification tag on said blood container parallely disposed to and in alignment with said blood container,
(g) means for removably connecting said blood container on said support parallely disposed to and in alignment with said first tag,
(h) means for filling said blood container with blood,
(i) means for mounting said support on the person of a user,
(j) said support is a band having
(k) means for engagement of the band about the wrist of the user,
(l) said means for mounting said first identification tag on said support including a pocket into which said tag is inserted,
(m) said means mounting said second identification tag on said blood container including a pocket into which said tag is inserted,
(n) said pocket mounting said first identification tag being transparent for viewing said first identification tag,
(o) said pocket mounting said second identification tag being transparent for viewing said second identification tag on said blood container,
(p) said first identification tag being exposed when said blood container is removed.

* * * * *